United States Patent [19]

Saitoh et al.

[11] 4,302,600
[45] Nov. 24, 1981

[54] PROCESS FOR THE PURIFICATION OF AN AQUEOUS ACRYLAMIDE SOLUTION

[75] Inventors: Jun Saitoh; Kenzo Fujii; Toshimi Nakagawa, all of Kamakura; Tadatoshi Honda, Fujisawa; Takatoshi Mitsuishi, Isehara; Hiroshi Itoh, Yokohama, all of Japan

[73] Assignee: Mitsui Toatsu Chemicals Incorporated, Tokyo, Japan

[21] Appl. No.: 151,777

[22] Filed: May 21, 1980

[30] Foreign Application Priority Data

May 28, 1979 [JP] Japan .................................. 54-64943

[51] Int. Cl.³ ........................................ C07C 103/133
[52] U.S. Cl. ................................................ 564/206
[58] Field of Search ........................................ 564/206

[56] References Cited

U.S. PATENT DOCUMENTS 2,865,960 12/1958 Shearer, Jr. et al. ............... 564/206
3,923,741 12/1975 Asano et al. ........................ 564/206
4,108,893 8/1978 Asano et al. ........................ 564/206

FOREIGN PATENT DOCUMENTS 50-82011 7/1975 Japan .
50-83323 7/1975 Japan .

Primary Examiner—John Doll

[57] ABSTRACT

A process for purifying an aqueous acrylamide solution which has been obtained by catalytic hydration of acrylonitrile with water in the presence of a copper-containing catalyst is disclosed, said process comprising passing said solution through a weakly basic anion exchange resin having primary and/or secondary amino groups, said resin being replaced with a new one after the use without regeneration.

4 Claims, No Drawings 4,302,600

PROCESS FOR THE PURIFICATION OF AN AQUEOUS ACRYLAMIDE SOLUTION

BACKGROUND OF THE INVENTION (1) Field of the Invention

This invention relates to an improvement in the purification of an aqueous acrylamide solution which has been obtained by the catalytic hydration of acrylonitrile with water in the presence of a copper-containing catalyst. The invention particularly concerns with a method for preparing an aqueous acrylamide solution useful as the starting material of a coagulating agent.

(2) Description of the Prior Art

Acrylamide is useful as a starting material of polyacrylamide which finds a wide variety of uses such as paper strengthening agent, coagulating agent, soil reforming agent and the like.

Acrylamide has been recently produced by catalytic hydration of acrylonitrile with water in the presence of a copper-containing catalyst. That process is extremely advantageous, because the product is obtained in the form of an aqueous solution and can be subjected to the polymerization reaction as is. If the aqueous acrylamide solution obtained upon the hydration is directly subjected to the polymerization reaction, however, high quality polyacrylamide cannot be obtained, probably due to the trace substances present in the solution, such as (1) unreacted acrylonitrile,
(2) metallic ions such as copper ion and complex ion formed with the copper, which are eluted from the catalyst component,
(3) impurities contained in the starting acrylonitrile and
(4) side reaction products such as an organic acid.

Of those substances, unreacted acrylonitrile can be easily removed by the practices known per se, such as distillation. Also the copper forming the metallic ion and copper complex ion can be removed, for example, by a treatment with H-form, or an ammonium salt form, strongly acidic cation exchange resin. It is difficult, however, to completely eliminate the organic matters forming the complex ions with copper, the traces of side reaction products and the impurities contained in the starting acrylonitrile, with such a strongly acidic cation exchange resin treatment alone.

As the means to cover the above shortcomings, three methods have been proposed. The first method proposes to treat the aqueous acrylamide solution obtained upon the catalytic hydration of acrylonitrile with a OH-form or a weak acid salt form, strongly basic anion exchange resin (Japanese Laid-Open Patent Publication No. 82011/1975). As the second method, it is known to treat the so obtained aqueous acrylamide solution with a mixed bed composed of a cation exchange resin and a strongly basic anion exchange resin. As the strongly basic anion exchange resin, "Diaion PA 316" (commercial product of Mitsubishi Kasei Kogyo K.K.), which is strongly basic, porous I form, is recommended (Japanese Laid-Open Patent Publication No. 83323/1975). As the third method, furthermore, it is known to treat the aqueous solution first with a strongly acidic cation exchange resin and then with a weakly basic anion exchange resin, and as the useful exchange resin for the second stage treatment, those containing primary, secondary, or tertiary amino groups are named (Japanese Laid-Open Patent Publication No. 91819/77). The literature disclosing the third method gives the experimental results using, as such amino group-containing resins, "Lewatit MP 62" (commercial product of Bayer A.G.) and "Diaion WA 10" (commercial product of Mitsubishi Kasei Kogyo K.K.), and names "Amberlite IRA-93" (commercial product of Rohm and Haas Co.) as an example. The exchange groups of those resins, however, are invariably tertiary amino groups. Thus absolutely no disclosure is found in the literature concerning the use of weakly basic anion exchange resins containing primary and/or secondary amino groups.

According to our studies, the aqueous acrylamide solution which has been purified by such known methods as above is quite satisfactory for making the polyacrylamide for a paper strengthening agent. The solution cannot be satisfactorily purified, however, to serve as the starting material of polyacrylamide as a coagulating agent, for example, and can hardly provide a coagulating agent showing good coagulating ability and water-solubility.

SUMMARY OF THE INVENTION

The primary object of the present invention is to provide a process for purifying an aqueous acrylamide solution which is obtained by catalytic hydration of acrylonitrile with water in the presence of a copper-containing catalyst, to a purity suitable for the starting material of polyacrylamide.

Another object of the invention is to provide an aqueous acrylamide solution which is useful for making a coagulating agent exhibiting excellent coagulating ability and water-solubility.

According to the present invention, the foregoing first and second objects can be accomplished by passing an aqueous acrylamide solution which has been obtained through catalytic hydration of acrylonitrile with water in the presence of a copper-containing catalyst, through a weakly basic anion exchange resin containing primary and/or secondary amino groups, said resin being replaced after use, not subjected to any regenerating treatment.

The process can be more economical, if it is practiced after passing the solution first through a strongly acidic cation exchange resin and second through a weakly basic anion exchange resin containing tertiary amino groups.

DETAILED DESCRIPTION OF THE PREFERRED EMBODIMENTS

The aqueous acrylamide solution to which the invention is to be applied is that obtained by catalytic hydration of acrylonitrile with water in the presence of a copper-containing catalyst.

As the copper-containing catalyst to be used in the acrylamide preparation, any of the heretofore known catalysts may be used, for example, (1) metallic copper in the form of wire or powder and copper ion,
(2) reduced copper obtained by reducing a copper compound such as cupric oxide, cupric hydroxide or a copper salt at a high temperature, e.g., 100°–400° C., with hydrogen or carbon monoxide,
(3) reduced copper obtained by treating in the liquid phase a copper compound such as cupric oxide, cupric hydroxide or a copper salt with a reducing agent such as hydrazine, an alkali metal or alkaline earth metal borohydride or formaldehyde, (4) reduced copper obtained by treating in the liquid phase a copper compund such as cupric oxide, cupric hydroxide or a copper salt with a metal exhibiting a stronger ionizing tendency than copper, such as zinc, aluminum, iron or tin, (5) Raney copper obtained by developing a Raney alloy composed of aluminum, zinc or magnesium and copper, (6) metallic copper obtained through pyrolysis of an organocopper compound such as cupric formate or cupric oxalate at a temperature ranging, for example, 100°–400° C., and (7) a pyrolyzed product of copper hydride. Those copper-containing catalysts may contain, in addition to the ordinarily employed supports, conventionally used metals other than copper, such as chromium, molybdenum and the like.

The reaction of acrylonitrile with water in the presence of such a copper-containing catalyst is normally practiced using almost completely optional ratio of water to the acrylonitrile, at 20°–200° C., preferably 50°–150° C., under atmospheric or an elevated pressure, on the catalyst bed which may be suspended or fixed, and either continuously or batchwise. The liquid phase reaction is effected, while preventing the contact of the reaction materials and the copper-containing catalyst with oxygen or an oxygen-containing gas.

Then the reaction liquid is normally distilled, so that the unreacted acrylonitrile in the liquid may be distilled off, and the liquid may be concentrated so as to contain approximately 30–50% by weight of acrylamide.

Thus obtained aqueous acrylamide solution is treated according to the present invention.

That is, the aqueous acrylamide solution obtained as above is passed through a weakly basic anion exchange resin layer which contains primary and/or secondary amino groups. The spent resin is discarded to be replaced by the fresh one, without any regenerating treatment. In a preferred embodiment, the solution is first treated with a strongly acidic cation exchange resin and then with a weakly basic anion exchange resin containing tertiary amino groups, before it is passed through the weakly basic anion exchange resin containing primary and/or secondary amino groups.

In preferred embodiments of the present invention, (A) a strongly acidic cation exchange resin which has been formed in the H form (B) a weakly basic anion exchange resin containing tertiary amino groups which has been formed in the OH form or a weak acid salt-form such as acetate, and (C) a weakly basic anion exchange resin containing primary and/or secondary amino groups which has been formed in the OH form or a weak acid salt form such as acetate, can be used in various combination, for example, (1) A–B–C, (2) A–C–B, or (3) A–C. With the above combinations (1) and (2), the treatment is run in such a manner that the cationic and anionic impurities would be removed mainly by A and B.

In the optimum embodiment the above combination (1) is selected mainly for economical reasons, to make the treating amount of the aqueous acrylamide solution per unit amount of the weakly basic anion exchange resin containing primary and/or secondary amino groups, the maximum. More specifically, the aqueous acrylamide solution is treated with a H form strongly acidic cation exchange resin A in the first stage, and with a free tertiary amino group-containing weakly basic anion exchange resin B in the second stage. In the third stage, furthermore, the solution is treated with a weakly basic anion exchange resin C containing free primary and/or secondary amino groups.

Ordinary ionic trace impurities are removed during the initial two stages, and the ion exchange resins used therein are regenerated by the accepted practice using an acid, alkali and the like, washed thoroughly with water, and re-used. The weakly basic anion exchange resin used in the third stage, on the other hand, is not regenerated, but is replaced by a new one at a suitable time.

According to our studies, the ion-exchange capacity of any ion exchange resin decreases with the time passage, from various reasons. The decrease is particularly conspicuous with the weakly basic anion exchange resin containing primary and/or secondary amino groups, compared with that of, for example, the weakly basic anion exchange resin containing tertiary amino groups. Although the components to be removed by the treatment of this invention have not been precisely identified, it is suggested that they are the compounds removable not by ion exchange mechanism but by certain other mechanism. This is the reason why the weakly basic anion exchange resin containing primary and/or secondary amino groups is renewed, with no regenerating treatment.

The contact of the aqueous acrylamide solution with the resin can be effected by using any of a suspended, fixed or moving bed system, a fixed bed being most frequently employed. The direction of the liquid flow through the resin bed may be ascending or descending. The passing temperature normally ranges 15°–60° C., at which the acrylamide is not degenerated, or precipitated as acrylamide crystals.

The ion exchange resins to be used in the invention can be selected from the presently commercialized products. As the weakly basic anion exchange resins containing primary and/or secondary amino groups, for example, Diaion WA-20, WA-21 and CR-20 (products of Mitsubishi Kasei Kogyo K.K.) may be named. Weakly basic anion exchange resins containing primary and/or secondary and tertiary amino groups may also be used, examples of which including Amberlite IR-45 (manufactured by Rohm & Haas Co.), Duolite A-2, A-4 and A-7 (manufactured by Diamond Shamrock Co.) and Dianion CR-40 (Mitsubishi Kasei Kogyo K.K.)

As the strongly acidic cation exchange resins to be regenerated and reused in the preferred embodiments of this invention, Amberlite IR-120B (Rohm & Haas Co.) and Lewatit SP 112 (Bayer AG) may be used. Also the specific examples of weakly basic anion exchange resin containing tertiary amino groups include Amberlite IRA-93 (Rohm & Haas Co.) and Lewatit MP62 (Bayer AG). The resin base may be gel or macroporous type.

As a mode of practice, the treatment of the present invention may be used as a pretreatment of polyacrylamide preparation. In such a practice, various known polymerization initiators normally can be used for the polyacrylamide preparation, for example, such azocompounds as azobisdimethylvaleronitrile, sodium salt of azobiscyanovaleric acid, azobisisobutyronitrile and azobisaminopropane hydrochloride; organoperoxides such as benzoyl peroxide, lauroyl peroxide and tert.butyl hydroperoxide; and inorganic peroxides such as potassium persulfate, sodium perbromide, ammonium persulfate and hydrogen peroxide. Also as the reducing agent to be used in the polymerization of acrylamide, such inorganic compounds as ferrous sulfate, ferrous chloride, sodium bisulfite, sodium metasulfite, sodium thiosulfate and nitrite; and such organic compounds as dimethylaniline, 3-dimethylaminopropionitrile and phenylhydrazine may be named.

In the process of this invention, the monomers useful for making the high molecular weight polymers are acrylamide and the mixtures of acrylamide and other monomer or monomers copolymerizable therewith. Examples of such copolymerizable monomers include methacrylamide, acrylic acid and salts thereof, N-methylacrylamide, N,N'-dimethylacrylamide, N-methylolacrylamide, 2-acrylamide-2-methylpropanesulfonic acid and salts thereof, aminoalcohol esters of methacrylic acid or acrylic acid (e.g., dimethylaminoethyl methacrylate and diethylaminoethyl acrylate) and their salts or quaternary ammonium salts, ester compounds of methacrylic acid or acrylic acid (e.g., methylmethacrylate and hydroxyethylacrylate) and acrylonitrile.

EXAMPLE 1

Preparation of crude aqueous acrylamide solution:

A reactor was charged with 70 parts by weight of Raney copper and 1000 parts of 25 wt% aqueous acrylonitrile solution, and the reaction was effected at 110° C. for 10 hours. After removing the catalyst in the reaction liquid by filtration, the reaction liquid was passed through a reduced pressure distillation. After thus distilling off the unreacted acrylonitrile and a part of water, a 33 wt% aqueous acrylamide solution was obtained. The acrylonitrile still remaining in the crude aqueous acrylamide solution was no more than 300 ppm, and the copper, no more than 80 ppm.

Purification of aqueous acrylamide solution:

The crude aqueous acrylamide solution was treated as follows: Three glass ion exchange columns (A, B and C) of each 20 mm in inner diameter and 50 cm in length were prepared. The column A was packed with 100 ml of a strongly acidic cation exchange resin, Amberlite IR 120B (Rohm & Haas Co.), which was regenerated in the H form and thoroughly washed with water. The column B was filled with 100 ml of a weakly basic anion exchange resin containing tertiary amino groups, Lewatit MP-62 (Bayer AG) which was kept in free form (OH form). The column C was filled with 100 ml of a weakly basic anion exchange resin containing primary and secondary amino groups, Amberlite IR 45 (Rohm & Haas Co.) which also was kept in free form (OH form). Then the three columns were connected in series as A–B–C, and the crude aqueous acrylamide solution was passed therethrough at 22° C., at a rate of "SV3" (300 ml/hr.), 0.96 m/hr.

Polymer preparation:

The aqueous acrylamide solution purified as above was adjusted of its acrylamide concentration to 20 wt% with distilled water. Into 100 parts each of the solution nitrogen was blown to expel the dissolved oxygen outside the system. Then the temperature of each system was adjusted to 30° C., and to which $22 \times 10^{-5}$ mol of ammonium persulfate as the catalyst and $1.0 \times 10^{-5}$ mol of sodium bisulfate as the assistant catalyst, each per mol of acrylamide, were added. The temperature of the system was allowed to rise as the exothermic polymerization reaction progressed. The system was let stand for an hour after the temperature rise became no more recognizable, and the polymerization was completed. The reaction product was composed of polyacrylamide and water, and was gel-like.

The gel-like product was crushed into the grains of each no greater than 2 mm in diameter, substituted with methanol, dried at 50° C. under reduced pressure and converted to polyacrylamide powder.

Evaluation of produced polymer:

The dry polymers obtained as above were evaluated as to their solubility in water and coagulating ability by the following methods. The results were given in Table 1.

(1) Solubility in water:

The dry polymer was made into a 0.1% aqueous solution and passed through a 200 mesh wire net. The water-insoluble portion was recovered, dried at 120° C. and its percentage by weight to the initially used polymer was calculated.

(2) Coagulating ability:

In this Example as well as Examples 2–5, Controls 1–5 and Referential Examples 1–2 and 4–5, a waste water formed by adding 400 ppm of aluminium sulfate to a kraft pulp waste water (pH 6.0) was used. Whereas, in Examples 6–7, Controls 6–7 and Referential Examples 3 and 6, a sludge formed from an activated sludge treatment of a waste water from foods industry (total solid content: 0.3%, pH 6.7) was used. That is, to either of the waste water, the dry polymers obtained as above was added at a weight ratio of 1 ppm, to cause flocculation or coagulation of the solid components in a jar tester accordingly to the accepted practices. The size of the so formed flocs was used as the norm for evaluating the polymer's coagulating ability.

EXAMPLES 2–7

The acrylamide produced and purified by the prosedures described in Example 1 was copolymerized with the monomers specified in Table 1, at the monomeric ratios also specified in the same table, in the manner described in Example 1. The resulting agar-like products were dried to provide powdery polymers, of which solubility in water and coagulating ability were duly evaluated. The results were as given concurrently in Table 1.

CONTROL 1–7

The aqueous acrylamide solution produced and purified similarly to Example 1 except that the purification column C was omitted, was copolymerized with the monomers at the ratios corresponding to those of Examples 2–7. Thus obtained powdery copolymers were evaluated of their solubility in water and coagulating ability similarly to the working Examples of this invention. The results are given also in Table 1.

Referential Examples 1–3

In the similar manner to Example 1, 105 liters of the crude aqueous acrylamide solution was passed through the three columns A, B and C which were connected in series. In the meantime, after passing each 10 liters of the solution, the resins in the columns A, B and C were regenerated by the practices known per se, i.e., the column A was treated with 2-N aqueous sulfuric acid, and the columns B and C, with 2-N aqueous sodium hydroxide. Thereafter the resins were washed thoroughly with water, and re-used repetitively. Of the so purified aqueous acrylamide solutions, the last 5 liters each was copolymerized with the monomers, at the ratios specified in Table 1. Thus obtained agar-like products were dried to provide powdery polymers. Using the powders, their solubility in water and coagulating ability were evaluated, with the results as shown in Table 1.

REFERENTIAL EXAMPLES 4-6

The columns A and B used in the Referential Examples 1-3 were connected with the column C which was filled with 100 ml of fresh Amberlite IR 45 (free form). The crude aqueous acrylamide solution was passed through the three columns similarly to Example 1. Thus obtained aqueous acrylamide solution was used to make the polymers from the monomeric compositions as specified in Table 1. The resulting polymers were evaluated of their solubility in water and coagulating ability, similarly to Example 1. The results were as given in Table 1.

TABLE 1

| Run No. | Monomeric Composition (mol %) Component A | | Component B | | water-solubility water-insoluble component (wt %) | coagulating ability waste | floc size (mm) |
|---|---|---|---|---|---|---|---|
| Example 1 | AAM | 100 | — | — | <0.1 | kraft pulp | 3-4 |
| 2 | " | 95 | Na-A | 5 | <0.1 | " | 3-4 |
| 3 | " | 95 | MAA | 5 | <0.1 | " | 4-5 |
| 4 | " | 97 | N-MAAM | 3 | <0.1 | " | 3-4 |
| 5 | " | 98 | 2-AMM-2-MPS-Na | 2 | <0.1 | " | 4-5 |
| 6 | " | 90 | DMAEMA | 10 | <0.1 | foods | 5-6 |
| 7 | " | 80 | DMAEMAEC | 20 | <0.1 | " | 4-5 |
| Control 1 | AAM | 100 | — | — | 7.0 | kraft pulp | no flocculation |
| 2 | " | 95 | Na-A | 5 | 2.2 | " | <1 |
| 3 | " | 95 | MAA | 5 | 5.8 | " | <1 |
| 4 | " | 97 | N-MAAM | 3 | 4.6 | " | <1 |
| 5 | " | 98 | 2-AAM-2-MPS-Na | 2 | 2.5 | " | 1-2 |
| 6 | " | 90 | DMAEMA | 10 | 6.5 | foods | <1 |
| 7 | " | 80 | DMAEMAEC | 20 | 5.2 | " | <1 |
| Referential Example 1 | AAM | 100 | — | — | 8.5 | kraft pulp | no flocculation |
| 2 | " | 95 | Na-A | 5 | 3.5 | " | <1 |
| 3 | " | 80 | DEAEAEC | 20 | 4.2 | foods | <1 |
| 4 | " | 100 | — | — | <0.1 | kraft pulp | 3-4 |
| 5 | " | 95 | Na-A | 5 | <0.1 | " | 3-4 |
| 6 | " | 80 | DEAEAEC | 20 | <0.1 | foods | 4-5 |

As is apparent from the results shown in Table 1, the polyacrylamide prepared from the acrylamide purified according to the present invention contained no more than 0.1 wt% of water-insoluble component, and showed excellent coagulating ability as demonstrated by the floc sizes of normally 3-6 mm. The flocs also exhibited good separability. In contrast thereto, in the experiments run omitting the column C, i.e., the specified weakly basic anion exchange resin treatment, the content of water-insoluble matter increased to nearly 10 wt%, and the floc size was small, such as no greater than 1 mm, which furthermore was difficult of separating. Also in the Referential Examples, it was demonstrated that the regenerating treatment of the column C is ineffective, the purification effect being reproduced only when the column C was replaced with new resin.

What is claimed is:

1. A process for the purification of a crude aqueous acrylamide solution obtained by catalytic hydration of acrylonitrile with water, through a dual treatment first with a strongly acidic cation exchange resin and then with a weakly basic anion exchange resin, which comprises passing the crude aqueous acrylamide solution through a bed of a strongly acidic cation exchange resin, followed by a bed of a weakly basic anion exchange resin containing tertiary amino groups, and further through a bed of a weakly basic anion exchange resin containing primary and/or secondary amino groups, said resin containing primary and/or secondary amino groups being discarded after its use without any regenerating treatment.

2. The process according to claim 1, in which the weakly basic anion exchange resin containing primary and/or secondary amino groups is formed in the OH forms or a weak acid salt form in advance.

3. The process according to claim 1, in which the aqueous solution is passed through the resin bed at 15°-60° C.

4. The process according to claim 1, in which the strongly basic cation exchange resin is formed in the H form in advance.